(12) United States Patent
Shimoyama et al.

(10) Patent No.: US 10,144,891 B2
(45) Date of Patent: *Dec. 4, 2018

(54) METHOD FOR PREPARING COAL MIXTURE FOR COKEMAKING, COAL MIXTURE, AND METHOD FOR PRODUCING COKE

(71) Applicant: JFE STEEL CORPORATION, Chiyoda-ku, Tokyo (JP)

(72) Inventors: Izumi Shimoyama, Kurashiki (JP); Takashi Anyashiki, Kawasaki (JP); Kiyoshi Fukada, Fukuyama (JP); Hidekazu Fujimoto, Kawasaki (JP); Hiroyuki Sumi, Kawasaki (JP)

(73) Assignee: JFE Steel Corporation, Tokyo (JP)

( * ) Notice: Subject to any disclaimer, the term of this patent is extended or adjusted under 35 U.S.C. 154(b) by 294 days.

This patent is subject to a terminal disclaimer.

(21) Appl. No.: 14/388,578

(22) PCT Filed: Mar. 25, 2013

(86) PCT No.: PCT/JP2013/001982
§ 371 (c)(1),
(2) Date: Sep. 26, 2014

(87) PCT Pub. No.: WO2013/145680
PCT Pub. Date: Oct. 3, 2013

(65) Prior Publication Data
US 2015/0040468 A1    Feb. 12, 2015

(30) Foreign Application Priority Data

Mar. 27, 2012 (JP) .................................. 2012-071517

(51) Int. Cl.
*C10L 5/04* (2006.01)
*C10B 57/04* (2006.01)
(Continued)

(52) U.S. Cl.
CPC ................ *C10L 5/04* (2013.01); *C10B 57/04* (2013.01); *C10L 2290/02* (2013.01);
(Continued)

(58) Field of Classification Search
USPC ..................................................... 44/607, 620
See application file for complete search history.

(56) References Cited

U.S. PATENT DOCUMENTS 4,135,983 A    1/1979 Kiritani
2013/0255142 A1    10/2013 Dohi

FOREIGN PATENT DOCUMENTS

JP    8-176553 A    7/1996
JP    2005-281355 A    7/1996
(Continued)

OTHER PUBLICATIONS

JP2005281355; Nagano et al.; Machine Translation of Abstract; Oct. 2005.*

(Continued)

*Primary Examiner* — Ellen M McAvoy
*Assistant Examiner* — Chantel L Graham
(74) *Attorney, Agent, or Firm* — RatnerPrestia

(57) ABSTRACT

Provided is a method for preparing a coal mixture used for the purpose of producing coke with desired strength by taking into account the compatibility between coals for cokemaking. In the case of preparing a coal mixture, used as at least one portion of a coal blend for cokemaking, containing two or more types of coals with different surface tensions, the blending ratio of each of the coals is adjusted using the surface tension of a semicoke mixture obtained from the coal mixture as an indicator.

15 Claims, 1 Drawing Sheet

(51) Int. Cl.
*G01N 33/22* (2006.01)
*G01N 13/02* (2006.01)

(52) U.S. Cl.
CPC .......... *C10L 2290/24* (2013.01); *G01N 13/02* (2013.01); *G01N 33/222* (2013.01)

(56) References Cited

FOREIGN PATENT DOCUMENTS

| JP | 09-255966 | | 9/1997 |
|----|-----------|---|--------|
| JP | 2005281355 | * | 10/2005 |
| JP | 2008069258 | | 3/2008 |
| WO | 2012029983 | | 3/2012 |
| WO | WO 2013/054526 A1 | | 4/2013 |

OTHER PUBLICATIONS

Niekerk et al., Blast-furnace coke: A coal-blending model, Journal of South African Inst. Min. Metall., 1991, vol. 91, No. 2, pp. 53-61.*
Japanese Office Action with partial English language translation for Application No. JP 2014-507421, dated Jan. 6, 2015, 3 pages.
European Search Report dated Dec. 7, 2015 for European Application No. 15002657.3-1559.
European Search Report dated Mar. 20, 2015 for European Application No. 13768491.6.
Forrest et al., "Theoretical and Experimental Approaches to the Carbonization of Coal and Coal Blends," Analytical Characterization Techniques, Nov. 12, 1982, vol. 205, pp. 1-25.
Oh et al., "An experimental and modeling study of softening coal pyrolysis," Aiche Journal, vol. 35, No. 5, May 1, 1989, pp. 775-792.
Dash et al,. "Laboratory scale investigation on maximising utilisation of carbonaceous inerts in stamp charging to improve coke quality and yield," Ironmaking & Steelmaking, vol. 34, No. 1, Jan. 1, 2007, pp. 23-29.
Miyazu, Okuyama, Suzuki, Fukuyama, and Mori, *Nippon Kokan Technical Report*, vol. 67, p. 1 (1975).
Sakamoto and Igawa, *CAMP-ISIJ*, vol. 11, p. 689 (1998).
International Search Report dated Jun. 11, 2013, application No. PCT/JP2013/001982 .
U.S. Final Office Action for U.S. Appl. No. 14/783,608, dated May 18, 2017, 20 pages.
Non Final Office Action for U.S. Appl. No. 14/783,608, dated Oct. 7, 2016, 16 pages.
Non Final Office Action for U.S. Appl. No. 14/387,734, dated Apr. 21, 2017, 21 pages.
Non Final Office Action for U.S. Appl. No. 14/387,742, dated Apr. 20, 2017, 23 pages.
Non Final Office Action for U.S. Appl. No. 14/351,745, dated Nov. 23, 2015, 32 pages.

* cited by examiner

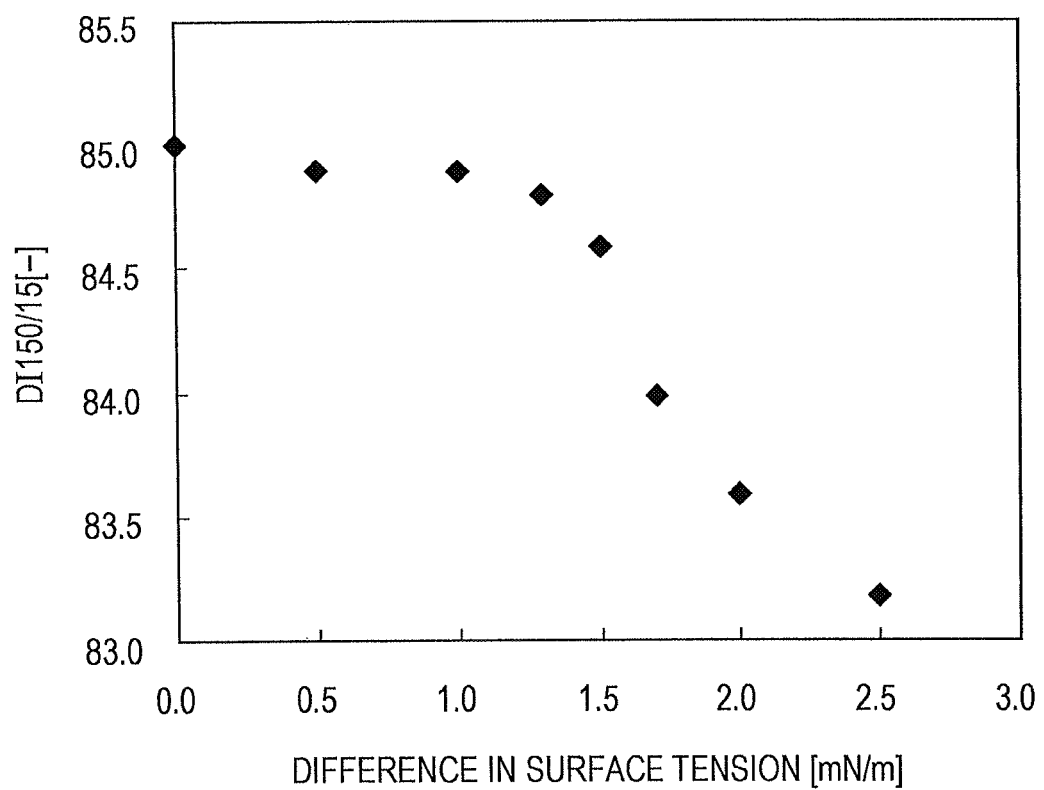

METHOD FOR PREPARING COAL MIXTURE FOR COKEMAKING, COAL MIXTURE, AND METHOD FOR PRODUCING COKE

CROSS REFERENCE TO RELATED APPLICATIONS

This is the U.S. National Phase application of PCT/JP2013/001982, filed Mar. 25, 2013, which claims priority to Japanese Patent Application No. 2012-071517, filed Mar. 27, 2012, the disclosures of each of these applications being incorporated herein by reference in their entireties for all purposes.

FIELD OF THE INVENTION

The present invention relates to a method for preparing coal mixtures for cokemaking, particularly relates to a method for preparing a coal mixture comprising: adjusting the blending ratio of coal contained in the coal mixture by taking into account the surface tension of a thermally treated product (hereinafter referred to as "semicoke") obtained by thermally treating the coal contained in the coal mixture. Furthermore, the present invention relates to a coal mixture produced by the preparation method and a method for producing coke by carbonizing the coal mixture.

BACKGROUND OF THE INVENTION

It is widely known that a coke with high strength is desirable for use as a raw material in the production of pig iron in a blast furnace. A coke with low strength would disintegrate in the blast furnace and deteriorate the gas permeability of the blast furnace, which leads to unstable production of pig iron.

In the case of producing coke for ironmaking by carbonizing coal in a horizontal chamber coke oven, the strength of produced coke is affected by the conditions such as a method for selecting coal for cokemaking, a preparation method, carbonization conditions, quenching conditions, post-treatment conditions. Among these conditions, conditions relating to facilities or operation are limited due to equipment and it is difficult to significantly change the conditions. Therefore, the selection of coal for cokemaking is recognized as the most important factor in controlling the coke properties.

Various methods are known for blending coals to produce a coke with desired strength, including a method described in Non Patent Literature 1. All of these method comprises predicting the strength of produced coke based on the properties of the coals to be blended and determining a blend of coals to provide high strength.

However, it is known that the conventional methods for determining the blend of coals provide inaccurate estimation of coke strength. In this case, the influence of an effect referred to as the "compatibility between coals" is conceivable. The "compatibility between coals" refers to the interaction between a plurality of coals in a coal blend. It is known that additivity does not hold between the strength of coke obtained from each coal in the coal mixture and the strength of coke obtained from the coal mixture because of the compatibility between the coals as disclosed in, for example, Patent Literature 1 and Non Patent Literature 2. If a mechanism creating the "compatibility" effect is clear, then coke with high-strength can be produced using a combination of compatible coals. However, conventional techniques have not clarified what creates the "compatibility" effect. It is unknown that what coal mixture should be supplied in order to achieve a combination of compatible coals or how to obtain such a coal mixture.

PATENT LITERATURE

PTL 1: Japanese Unexamined Patent Application Publication No. 9-255966

NON PATENT LITERATURE

NPL 1: Miyazu, Okuyama, Suzuki, Fukuyama, and Mori, *Nippon Kokan Technical Report*, volume 67, page 1 (1975)

NPL 2: Sakamoto and Igawa, *CAMP-ISIJ*, volume 11, page 689 (1998)

SUMMARY OF THE INVENTION

There is a lot of uncertainty about the compatibility between coals as described above. In this regard, it is an object of the present invention to provide a method for preparing a coal mixture used to produce coke with desired strength by taking into account the compatibility between coals for cokemaking. Furthermore, it is an object of the present invention to provide a coal mixture produced by the preparation method and a method for producing coke by carbonizing the coal mixture.

In order to solve the above problems, the inventors have investigated various methods by taking into account the surface tension of coal that has not been taken into account in conventional coke production techniques or the surface tension of semicoke obtained by thermally treating coal. As a result, the inventors have found that the effect of the compatibility between coals can be desirably created using the difference in surface tension between semicokes obtained from a plurality of coals. In addition, the inventors have found a method for adjusting the surface tension of semicoke to a desired value and a method for selecting the desired value to complete the present invention.

Aspects of the present invention for solving the above problems are as described below.

(1) A method for preparing a coal mixture for cokemaking, the coal mixture containing two or more types of coals with different surface tensions, the coal mixture being used as at least one portion of a coal blend for cokemaking,
the method includes:
adjusting a blending ratio of each of the coals using surface tension of a semicoke mixture obtained from the coal mixture as an indicator.

(2) In the method for preparing the coal mixture for cokemaking as specified in Item (1), the surface tension of the semicoke mixture is a value that is determined by weighted-averaging the surface tensions of two or more types of semicokes using the blending ratios of the coals in the coal mixture as weights, the two or more types of semicokes being obtained by thermally treating the coals contained in the coal mixture.

(3) In the method for preparing the coal mixture for cokemaking as specified in Item (1) or (2), the blending ratio of each coal contained in the coal mixture is adjusted such that the surface tension of the semicoke mixture is within the range of ±1.5 mN/m from a surface tension of semicoke obtained by thermally treating the rest of the coal blend excluding the coal mixture.

(4) In the method for preparing the coal mixture for cokemaking as specified in Item (3), the surface tension of the semicoke obtained by thermally treating the rest of the coal blend is a value that is determined by weighted averaging the surface tensions of semicokes obtained by thermally treating at least two types of coals contained in the rest of the coal blend using the blending ratios of the at least two types of coals contained in the rest of the coal blend as weights.

(5) In the method for preparing the coal mixture for cokemaking as specified in Item (3), the surface tension of the semicoke obtained by thermally treating the rest of the coal blend is a surface tension of semicoke obtained by thermally treating one type of coal of at least one type of coal contained in the rest of the coal blend, the content of the one type of coal being highest.

(6) In the method for preparing the coal mixture for cokemaking as specified in Item (3), the surface tension of the semicoke obtained by thermally treating the rest of the coal blend is a value that is determined by weighted-averaging the surface tensions of plural types of semicokes using the blending ratios of plural types of coals as weights, the plural type of semicokes being obtained by thermally treating the plural types of coals contained in the rest of the coal blend, the sum of the mass contents of the plural types of coals being 50% by mass or more.

(7) In the method for preparing the coal mixture for cokemaking as specified in Item (1) or (2), the blending ratio of each coal in the coal mixture is adjusted such that the semicoke mixture has such a surface tension that the interfacial tension between the semicoke mixture and semicoke obtained by thermally treating one type of coal of at least one type of coal contained in the rest of the coal blend, excluding the coal mixture, for cokemaking, the mass content of the one type of coal being 50% by mass or more, is 0.03 mN/m or less.

(8) In the method for preparing the coal mixture for cokemaking as specified in Item (7), the interfacial tension is calculated by Equation (2).

[Math. 2]

$$\gamma_{AB} = \gamma_A + \gamma_B - 2\phi\sqrt{\gamma_A\gamma_B} \quad (2)$$

Herein, $\gamma_A$ is a surface tension of the semicoke obtained by thermally treating the one type of coal, $\gamma_B$ is a surface tension of the semicoke mixture, $\gamma_{AB}$ is a interfacial tension, and $\phi$ is an interaction coefficient.

(9) In the method for preparing the coal mixture for cokemaking as specified in Item (7), the interfacial tension is calculated by Equation (3).

[Math. 3]

$$\gamma_{AB} = \gamma_A + \gamma_B - 2\exp[-\beta(\gamma_A-\gamma_B)^2]\sqrt{\gamma_A\gamma_B} \quad (3)$$

Herein, $\gamma_A$ is a surface tension of the semicoke obtained by thermally treating the one type of coal, $\gamma_B$ is a surface tension of the semicoke mixture, $\gamma_{AB}$ is a interfacial tension, and $\beta$ is a constant.

(10) In the method for preparing the coal mixture for cokemaking as specified in Item (1) or (2), the blending ratio of each coal in the coal mixture is adjusted such that the semicoke mixture has such a surface tension that the interfacial tension between the semicoke mixture and plural types of semicokes obtained by thermally treating plural types of coals in the rest of the coal blend, excluding the coal mixture, for cokemaking, the sum of the mass contents of the plural types of coals being 50% by mass or more, is 0.03 mN/m or less.

(11) In the method for preparing the coal mixture for cokemaking as specified in Item (10), the interfacial tension is calculated by Equation (2).
Herein, $\gamma_A$ is a surface tension of the plural types of semicokes, $\gamma_B$ is a surface tension of the semicoke mixture, $\gamma_{AB}$ is the interfacial tension, and $\phi$ is an interaction coefficient.

(12) In the method for preparing the coal mixture for cokemaking as specified in Item (10), the interfacial tension is calculated by Equation (3).
Herein, $\gamma_A$ is a surface tension of the plural types of semicokes, $\gamma_B$ is the surface tension of the semicoke mixture, $\gamma_{AB}$ is a interfacial tension, and $\beta$ is a constant.

(13) A method for preparing a coal mixture for cokemaking, the coal mixture containing two or more types of coals, the coal mixture being used as at least one portion of a coal blend for cokemaking, includes:

determining a blending ratio of the coal mixture in the coal blend in advance in the case of using the coal mixture being as a portion of the coal blend, determining a type and a blending ratio of coal contained in the rest of the coal blend excluding the coal mixture, and adjusting the blending ratio of each coal in the coal mixture such that the interfacial tension ($\gamma_{blend}$) of semicoke obtained by thermally treating the coal blend is 0.03 mN/m or less.

(14) In the method for preparing the coal mixture for cokemaking as specified in any one of Items (1) to (13), the interfacial tension is determined by a film floatation method.

(15) A coal mixture is produced by the preparation method specified in any one of Items (1) to (14).

(16) A method for producing coke includes preparing a coal blend containing the coal mixture specified in Item (15) and carbonizing the coal blend.

The present invention is based on the fact that the surface tension of a semicoke mixture obtained by thermally treating a coal mixture containing two or more types of coals indicates the compatibility between coals and has been completed on the basis of a method for preparing the coal mixture using the surface tension thereof as an indicator.

The present invention can provide a coal mixture which is a preferred raw material for producing coke with desired strength. In addition, a coal mixture preferably used as at least one portion of a raw material for coke can be prepared.

Furthermore, the present invention has an effect that in the case of using a coal mixture containing a plurality of coals as a portion of a coal blend for cokemaking, even when properties of coal contained in the rest of the coal blend excluding the coal mixture are not all clear, the blending ratios of the coals in the coal mixture can be adjusted in order to produce coke with desired strength.

BRIEF DESCRIPTION OF DRAWING

FIG. 1 is a graph showing the relationship between the difference in surface tension and the strength of produced coke.

DETAILED DESCRIPTION OF EMBODIMENTS OF THE INVENTION

The inventors have inferred that the adhesion phenomena of coal affects the compatibility between coals and the strength of coke, and have investigated factors relating to the adhesion of coal on the basis of this inference. As the result, the inventors have found that it is possible to adjust the adhesion strength of the coal mixture by adjusting the blending ratio of coals using the surface tension of a semicoke mixture obtained from a coal mixture as an indicator. In particular, the inventors have obtained a finding that in the case of using the semicoke mixture as a portion of a coal blend for cokemaking, the adhesion strength between coals can be increased by adjusting the blending ratio of each coal in the coal mixture such that the surface tension of the semicoke mixture falls within a specific range from the surface tension of semicoke obtained from coal contained in the rest of the coal blend excluding the coal mixture.

The above finding is described below in detail. In general, it is known that when two substances with different surface tensions adhere to each other, the smaller the difference in surface tension therebetween is, the higher the adhesion strength therebetween is. In the course of coking, coal is melted once by heating and is then solidified, whereby coke is produced. In this course, different coals need to adhere to each other to form a strong coke structure. In a conventional idea, the strong coke structure is probably formed by the fusion of coals and plastic properties (for example, the Gieseler maximum fluidity MF) of coal probably take important roles.

In contrast to the idea, the inventors have experimentally confirmed the relationship between the difference in surface tension between semicokes obtained by thermally treating different coals and the strength of coke. In addition, since the interfacial tension between the adhering substances is expressed by the difference in surface tension therebetween, the inventors have experimentally confirmed the interfacial tension and the coke strength.

In the case of investigating the above adhesion phenomenon, it is probably preferred that the surface tension of plastic coal is determined at temperatures of 350° C. to 800° C. at which coals actually begin to become plastic and adhere to each other to form solids, thereby completing coking, and the value of the surface tension is used. However, a method for measuring the surface tension at such high temperature range has not been known. Therefore, the inventors have investigated various methods. As a result, the inventors have found that the surface tension of coal in a plastic state can be estimated by measuring the surface tension of semicoke that is carbonized by heating the coal to a temperature at which the coal becomes plastic, followed by cooling.

From an idea that the surface tension affects the adhesion between coal particles, it is probably appropriate that the heating temperature of the coals is in a temperature range up to a coking temperature at which the coals begin to become plastic and adhere to each other to form solids, thereby completing coking, that is, from 350° C., at which the coals begin to become plastic, to 800° C., at which coking is completed. However, in the heating temperature of from 350° C. to 800° C., the temperature that particularly contributes to adhesion is 350° C. to 550° C., at which the coals become plastic. An adhesion structure probably determines at near 500° C. Therefore, the heating temperature is preferably near 500° C., particularly 480° C. to 520° C. Incidentally, heating is preferably performed in an atmosphere of an inert gas (for example, nitrogen, argon, helium, or the like) not reactive with the coals.

Cooling is preferably performed in an atmosphere of an inert gas not reactive with a sample. In addition, in the cooling of the carbonized coals, quenching is preferably performed at a cooling rate of 10° C./sec or more. A reason for quenching is that a molecular structure is maintained in a plastic state. A cooling rate of 10° C./sec or more is necessary because the molecular structure does not probably vary. As a quenching method, a method using liquid nitrogen, ice water, water, an inert gas such as a nitrogen gas, or the like is known. Quenching is preferably performed using liquid nitrogen. This is because gas cooling takes a long time to cool an inner portion of a sample and causes a cooling rate distribution or ice water or water cooling affects the measurement of the surface tension because of the adhesion of moisture.

That is, in the present invention, exemplary operations for thermally treating coal are as described below.

(a) Coal is crushed. From the viewpoint of preparing a homogeneous sample from coal uneven in structure, properties, or the like, the coal is preferably crushed to a particle size of 250 μm or less as specified in the proximate analysis of coal described in JIS M 8812 and more preferably 200 μm or less.

(b) The coal crushed in Operation (a) is heated at an appropriate heating rate in the absence of air or in an inert gas. The coal may be heated to a temperature of 350° C. to 800° C. as described above. The heating rate thereof is most preferably determined depending on the heating rate used in producing coke in a coke oven.

(c) The coal heated in Operation (b) is cooled. In this cooling, quenching is preferably performed by the above-mentioned method.

A method for measuring the surface tension of a substance is described below. As a method for measuring the surface tension, the following methods are known: a sessile drop method, a capillary-rise method, a maximum bubble pressure method, a drop weight method, a pendant drop method, a ring method, the Wilhelmy method, an advancing/receding contact angle method, a tilting plate method, and the like. Since coal is composed of various molecular structures and it is conceivable that the surface tension thereof is not even, a method capable of evaluating the distribution of surface tension, for example, a film floatation method (refer to D. W. Fuerstenau, *International Journal of Mineral Processing*, 20 (1987), 153) can be used. This method can be evenly applied to coal and semicoke obtained from this coal and can evaluate the distribution of surface tension using a crushed sample. The average of the distribution of obtained surface tensions can be regarded as the typical surface tension of the sample. In the case of using semicoke as a sample, the thermal treatment temperature during the heating of coal is preferably set to the thermoplastic temperature range of the coal.

The measurement of surface tension by the film floatation method is preferably performed as described below. Since the surface tension of coal in a plastic state is distributed within the range of 20 mN/m to 73 mN/m, a liquid with a surface tension within this range may be used in the film floatation method. For example, organic solvents such as ethanol, methanol, propanol, tert-butanol, and acetone can be used to prepare liquids with a surface tension of 20 mN/m to 73 mN/m from aqueous solutions of these organic solvents. The particle size of a sample measured for surface tension is as follows: the sample is preferably crushed to a particle size of 53 μm to 150 μm, because the surface tension is preferably measured at a contact angle substantially equal to 0° from measurement principles, the particle size of the crushed sample is preferably small since the contact angle increases with the increase in particle size thereof, and the sample particles are likely to be aggregated when the particle size is less than 53 μm. The sample particles are dropped in liquids with various surface tensions, the mass percentage of the sample particles suspended in each liquid is determined, and the results are plotted on a frequency distribution curve, whereby the surface tension distribution can be obtained.

An example of a method for preparing semicoke used as a sample for the film floatation method is described below.
1. Coal is crushed to a particle size of 200 μm or less and is then heated to 500° C. at 3° C./min in an inert gas atmosphere (carbonizing operation). The heating rate is 3° C./min because the heating rate of coke produced in a coke oven is about 3° C./min.
2. The heated coal is quenched with liquid nitrogen (cooling operation).
3. The quenched coal is further crushed to a particle size of 150 μm or less and is then dried at 120° C. for 2 hours in a flow of a dry inert gas (drying operation). Incidentally, a drying method may be any method capable of removing moisture attached to a surface. For example, a method of heating to 100° C. to 200° C. in an inert gas such as nitrogen or argon, vacuum drying, a method of drying at reduced pressure, and the like can be used. Incidentally, the dry inert gas can be obtained by feeding gas through a packed bed of a desiccant such as silica gel.

As an indicator of the surface tension, the average of the surface tension distribution obtained as described above can be used and the standard deviation of a surface tension distribution, the peak surface tension of a surface tension distribution, the maximum surface tension and minimum surface tension of a surface tension distribution, the distribution function of a surface tension distribution, and the like can be also used. In the present invention, the surface tension of coal or semicoke refers to the average of a surface tension distribution. The average (the average of γ: $\gamma_{ave}$) of a surface tension distribution is represented by an equation below.

[Math. 1]

$$\gamma_{ave} \int \gamma f(\gamma) d\gamma \quad (1)$$

In Equation (1), γ is the surface tension and f(γ) is the frequency of a surface tension distribution.

In the case of directly using coal as a sample for the film floatation method, coal not subjected to 1. carbonizing operation or 2. cooling operation but subjected to 3. drying operation may be used as a sample.

As a result of measuring the surface tension of coal and semicoke by the above-mentioned measurement method and performing intensive investigations, the inventors have found that the smaller the interfacial tension between coals or semicokes blended in a coal blend for cokemaking, that is, the smaller the difference in surface tension therebetween is, the higher the strength of coke tends to be. On the basis of this, it is inferred that coals (semicokes) with close surface tensions are preferably used as raw materials for coke so that the interfacial tension between different coals is reduced (the difference in surface tension therebetween is reduced). The inventors have thought that if a favorite is selected from given coal brands (types) on the basis of this inference and the surface tension of selected coal or semicoke obtained from the coal is adjusted, then coke with higher strength can be produced rather than selecting coal for cokemaking from only brands or types given by coal suppliers without taking into account the effect of the surface tension.

Therefore, the inventors have investigated means for adjusting the surface tension of semicoke and coal supplied from coal suppliers. In the course of this investigation, the inventors have focused on the fact that supplied coal is handled as a single brand or type of coal and however is actually a mixture of coals produced from a plurality of coal seams and have investigated the surface tension of semicokes obtained by the thermal treatment of the coals produced from the plurality of coal seams. As a result, the inventors have found that even similar grades of coals produced from a single mine are significantly different in surface tension in many cases. This shows that coal which has been handled as a single brand or type of coal is a mixture of products from coal seams having similar properties in terms of conventional grade evaluation indicators (coal rank, fluidity, composition, and the like) and however includes coals far from similar in quality in terms of an indicator that is the surface tension which has not been taken into account. It has become clear that if the surface tension of semicoke obtained from coal of each coal seam of a coal mine is measured on the basis of this fact and the blending ratio thereof is determined, then the surface tension of semicoke obtained from a single brand or type of coal can be adjusted with conventional grade indicators maintained. Incidentally, it has become clear that the surface tension of coal correlates with the strength of coke. However, since it has become clear that the surface tension of semicoke correlates with the strength of coke rather than the surface tension of coal, the surface tension of semicoke is used to estimate the strength of coke rather than the surface tension of coal in the present invention.

In the case of preparing a coal mixture, in a method for adjusting the blending ratio of coals using the surface tension of a semicoke mixture obtained from the coal mixture as an indicator, for example, a value determined by weighted-averaging the surface tensions of two or more types of semicokes obtained by thermal treating coals making up the coal mixture can be used for the surface tension of the semicoke mixture.

A method for adjusting the blending ratio of coals in a coal mixture on the basis of a value determined by weighted-averaging is, for example, as described below.
1. Determine, for example, a coal mixture to be composed of Coal A and Coal B. Assume a coal mixture prepared by mixing Coal A with Coal B. Suppose that the surface tension of semicoke obtained from Coal A, which is obtained from a coal seam, is a and the surface tension of semicoke obtained from Coal B, which is obtained from another coal seam, is b.
2. Assume the blending ratios of Coal A and Coal B in the assumed coal mixture.
3. Determine the mass-weighted-average of the surface tensions of Semicoke A obtained by thermal treating Coal A and Semicoke B obtained by thermal treating Coal B using the assumed blending ratios as weights. For example, in the case of a coal mixture prepared by mixing equal amounts of Coal A and Coal B, the mass-weighted-average of the surface tension obtained therefrom is given by (a+b)/2.
4. Suppose a value determined in Item 3 is the surface tension of a semicoke mixture, because this value is substantially equal to the surface tension of the semicoke mixture. The blending ratios of coals obtained from coal seams may be determined using the surface tension of the semicoke mixture as an indicator. That is, in the case of preparing the coal mixture, the blending ratio of each coal in the coal mixture may be adjusted.

The mixing ratio (blending ratio) may be adjusted by actually measuring the surface tension of the semicoke mixture obtained by thermally treating the coal mixture as required. The surface tension of the semicoke mixture is determined as the weighted-average of the surface tensions of semicokes obtained from the coals using the blending ratios of the coals in the coal mixture as weights or is determined by actually measuring the surface tension of the semicoke mixture obtained from the coal mixture.

In the present invention, a brand of coal is defined as a unit of coal, managed as a single lot, for cokemaking. The expression "managed as a single lot" includes the case where typical analytical values of a sample from the lot is used to express properties of the whole lot, the case of depositing a single lot on a coal yard, the case of putting a single lot in a coal bunker, the case of dealing a single lot or brand in a purchase agreement, and the like. In the present invention, the term "coal mixture" refers to a coal mixture prepared by mixing two or more types of coals with different surface tensions. For example, a coal mixture prepared by mixing two or more types of coals obtained from different coal seams may possibly be handled as a single brand of coal or a coal mixture may be prepared by mixing several brands of coals. Furthermore, in the present invention, the term "semicoke mixture" refers to semicoke obtained by thermally treating a coal mixture. Incidentally, in the present invention, a coal mixture may be prepared in a stage prior to delivering coal to a cokemaking plant. If a coal mixture with predetermined quality is prepared prior to delivery to a coking plant, for example, in a coal mine or at delivery from a delivery site, then the loads of blending management, transportation, and storage are reduced.

The following method is described in detail below: a method for adjusting the blending ratio of each coal in a coal mixture in the case of using the coal mixture for a coal blend by taking into account the surface tension of a semicoke mixture that is adjusted as described above as an indicator. Incidentally, in order to obtain the surface tension of the semicoke mixture, the surface tensions of semicokes obtained by thermally treating all the coals and the coal mixture under the same thermal treatment conditions are preferably used. Herein, the term "same thermal treatment conditions" means that the temperature, the time, an atmosphere, and the like are the same. For temperatures, characteristic temperatures (for example, the maximum fluidity temperature and the solidification temperature) of plasticity can be used. In the present invention, a value that needs to be taken by the surface tension of the coal mixture or the semicoke mixture ranges from 20 mN/m to 60 mN/m.

In the case of using the coal mixture as at least one portion of a coal blend for cokemaking, a target value that needs to be taken by the surface tension A of a semicoke mixture obtained from the coal mixture is determined depending on coal contained in the rest of the coal blend excluding the coal mixture in the coal blend when the coal blend for cokemaking is prepared. That is, it is preferred that at least one type of coal contained in the rest of the coal blend is determined, the surface tension B of semicoke obtained from the coal contained in the rest of the coal blend is measured, and the blending ratio of each coal contained in the coal mixture is adjusted such that the surface tension A falls within the range of ±1.5 mN/m from the surface tension B. Incidentally, in the case where the coal mixture is contained in the coal blend in the form of at least one portion of the coal blend, the content of the coal mixture in the coal blend is 2.0% to 98.0% by mass. When the content of the coal mixture is 2.0% to 98.0% by mass, the interaction between the coal mixture and the rest of the coal blend probably affects the strength of coke. Therefore, the present invention is meaningful in that the strength of coke is maintained by keeping the difference between the surface tension A and the surface tension B within a predetermined range.

The inventors have investigated various blends. As a result, it has been recognized that when the difference between the surface tension A and the surface tension B is more than 1.5 mN/m, the strength of produced coke is significantly reduced. A target value of the surface tension A of the semicoke mixture is based on this recognition. Adjusting the surface tension A to be close to the surface tension B allows coke to have increased strength as compared to coke obtained in the case where the surface tension A is not close to the surface tension B. This is preferred for raw materials for cokemaking.

Herein, the surface tension A or B may be a value that is determined by weighted-averaging the surface tensions of semicokes obtained from two or more types of coals making up the coal mixture or the rest of the coal blend using the blending ratio of each coal as a weight or may be a surface tension obtained by measuring semicoke obtained by thermally treating the coal mixture or the rest of the coal blend. Furthermore, in particular, in the case where the blending ratios of coals are close to each other, a simple average may be used as an indicator in addition to a weighted-average.

In the case of preparing semicoke from the coal mixture or the rest of the coal blend and actually measuring the surface tension thereof, the surface tension of the semicoke needs to be measured with every change in the blending ratio of coal in the coal mixture or the rest of the coal blend. On the other hand, in the case of adjusting the blending ratio of coal using a value determined by weighted-averaging as an indicator as described above, semicokes obtained from the coals making up the coal mixture or the rest of the coal blend are measured for surface tension in advance and a weighted-average can be calculated on a desk using the blending ratios of the coals making up the coal mixture or the rest of the coal blend as weights. Therefore, there is an advantage in that the manpower for actual measurement is not necessary.

Upon adding the coal mixture to the coal blend for cokemaking, there is a case where the coal mixture needs to be prepared in such a state that components of the coal blend other than the coal mixture are not all known. In this case, the surface tension B of the semicoke obtained from the coal contained in the rest of the coal blend may be estimated on the basis of, for example, a track record of using a coal brand in the plant over the past several months to years. A weighted-average may be calculated from the estimated surface tension.

In addition, in the case where the blending ratio of only one or some of the coals contained in the rest of the coal blend and the surface tension of semicoke obtained from the coal are known, the blending ratio of each coal in the coal mixture is preferably adjusted such that the surface tension A of the semicoke mixture falls within the range of ±1.5 mN/m from the surface tension B of semicoke obtained from a single type (a type) of coal that is most dominant among the coals contained in the rest of the coal blend. Incidentally, in this case, at least one type of coal is contained in the rest of the coal blend.

Furthermore, the blending ratio of each coal in the coal mixture may be adjusted such that the surface tension A of the semicoke mixture falls within the range of ±1.5 mN/m from a value that is determined by weighted-averaging the surface tensions of semicokes obtained from several types of coals of which the total mass content is 50% by mass or more using the blending ratios of the coals contained in the rest of the coal blend as weights, the total mass content being obtained by summing the mass contents from a range where the blending ratios and surface tensions of the coals contained in the rest of the coal blend. Supposing, for example, three brands of coals are known to be contained in the rest of the coal blend and the mass content of each type is 20%, the mass contents of these types of coals total 60% (20%×3), that is, 50% or more. In this case, the weighted-average of the surface tensions of semicokes obtained from the three types of coals is a target value of the surface tension A of the semicoke mixture. Coke obtained from a coal blend obtained in such a way has increased strength.

By taking into account the interfacial tension instead of the surface tension of the semicoke mixture, the blending ratio of each coal in the coal mixture can be adjusted using the interfacial tension between the semicokes obtained from the coals contained in the rest of the coal blend and the semicoke mixture obtained from the coal mixture as an indicator or using the interfacial tension of semicoke obtained from the coal blend as an indicator.

While the interfacial tension between two types of substances can be measured, the interfacial tension can be determined from the surface tension of each substance. For example, for different Substances A and B, the interfacial tension $\gamma_{AB}$ between Substances A and B can be determined from the surface tension $\gamma_A$ of Substance A and the surface tension $\gamma_B$ of Substance B and is represented by the Girifalco-Good equation below.

[Math. 2]

$$\gamma_{AB} = \gamma_A + \gamma_B - 2\phi\sqrt{\gamma_A \gamma_B} \quad (2)$$

In Equation (2), $\phi$ is an interaction coefficient. The interaction coefficient $\phi$ can be determined from experiments and is known to differ between the Substances A and B. Furthermore, D. Li and A. W. Neumann have supposed that the interaction coefficient $\phi$ increases with the increase in difference between the surface tensions $\gamma_A$ and $\gamma_B$ of Substances A and B and have proposed an equation which is an extension of Equation (2) as shown below.

[Math. 3]

$$\gamma_{AB} = \gamma_A + \gamma_B - 2\exp[-\beta(\gamma_A - \gamma_B)^2]\sqrt{\gamma_A \gamma_B} \quad (3)$$

In Equation (3), $\beta$ is a constant derived from experiments. D. Li and A. W. Neumann have calculated $\beta$ to be 0.0001247 $(m^2/mJ)^2$. Thus, supposing Substance A is Semicoke A obtained from Coal A and Substance B is Semicoke B obtained from Coal B, the interfacial tension $\gamma_{AB}$ between Semicokes A and B can be derived in such a way that the surface tensions $\gamma_A$ and $\gamma_B$ of Semicokes A and B are determined and are substituted into Equation (2) or (3). In the case of using Equation (2), the interaction coefficient $\phi$ needs to be determined from experiments. Therefore, Equation (3), in which interaction coefficient $\phi$ is estimated, is preferably used in the sense that the derivation of the surface tension is simplified.

Herein, in the case of preparing the coal mixture by taking into account the interfacial tension, supposing the surface tension of semicoke obtained from the rest of the coal blend is $\gamma_A$ and the surface tension of semicoke obtained from the coal mixture is $\gamma_B$, the interfacial tension can be calculated by Equation (2) or (3). As the surface tension of the semicoke obtained from the rest of the coal blend, supposing the surface tension of semicoke obtained from the one type of coal in the rest of the coal blend, the mass content of the one type of coal being 50% by mass or more, is $\gamma_A$ and the surface tension of the semicoke mixture is $\gamma_B$, the interfacial tension $\gamma_{AB}$ between the semicoke obtained from the one type of coal and the semicoke mixture is calculated.

Alternatively, as the surface tension of the semicoke obtained from the rest of the coal blend, supposing a value that is obtained by weighted-averaging the surface tensions of several types of semicokes obtained from several types of coals of which the total mass content is 50% by mass or more using the blending ratios of the several types of coals as weights is $\gamma_A$ or a value obtained by measuring the surface tension of the several types of semicokes is $\gamma_A$ and the surface tension of the semicoke mixture is $\gamma_B$, the interfacial tension $\gamma_{AB}$ between the several types of semicokes and the semicoke mixture can be calculated.

The blending ratio of each coal in the coal mixture is preferably adjusted by calculating the interfacial tension between the semicoke obtained from the one type of coal and the semicoke mixture obtained from the coal mixture or the interfacial tension between the several types of semicokes obtained from the several types of coals and the semicoke mixture as described above such that the semicoke mixture has such a surface tension that the interfacial tension therebetween is 0.03 mN/m or less.

Furthermore, when the types and blending ratios of the coals in the rest of the coal blend are known, the interfacial tension of semicoke obtained from the coal blend can be calculated. In the case where n types of coals are present in the coal blend, supposing the blending ratio thereof is $w_i$ (which represents the blending ratio of 1, 2, ..., i, ..., or n coal), the existence probability of an i-j interface formed by semicoke obtained from i coal and semicoke obtained from j coal is represented by the product of $w_i$ and $w_j$. Therefore, supposing the interfacial tension between these semicokes is $\gamma_{ij}$, the interfacial tension $\gamma_{blend}$ between these semicokes can be represented by an equation below. Incidentally, $w_i$ and $w_j$ are preferably represented with the blending ratios of the semicokes in the semicoke mixture in principle. However, the abundance of the semicoke obtained from each coal in the semicoke mixture does not differ significantly from the abundance of the coal in the coal blend. Therefore, $w_i$ and $w_j$ are represented with the blending ratios of the coals in the coal blend.

[Math. 4]

$$\gamma_{blend} = \sum_{i=1}^{n} \sum_{j=1}^{n} w_i w_j \gamma_{ij} \quad (4)$$

In the case of preparing the coal mixture by taking into account the interfacial tension of the semicoke obtained from the coal blend, the blending ratio of each coal in the coal mixture is adjusted by a procedure below.

1. Determine the blending ratio of the coal mixture in the coal blend and also determine the number n of the types of coals contained in the rest of the coal blend and the blending ratio $w_i$ to let the types and blending ratios of the coals in the rest of the coal blend to be known.

2. Determine the interfacial tension $\gamma_{ij}$ at the interface between the semicokes obtained from i coal and j coal. The interfacial tension can be determined by Equation (2) or (3).

3. Determine the interfacial tension $\gamma_{blend}$ of the semicoke obtained from the coal blend using above Equation (4). The blending ratio of each coal in the coal mixture can be adjusted such that the interfacial tension $\gamma_{blend}$ of the semicoke obtained from the coal blend is 0.03 mN/m or less. This enables coke with high strength to be produced.

It is ideal that the blending ratios of all coals used and the surface tensions of semicokes obtained from the coals are known. However, in the case of preparing a raw-material purchase or production plan, the ratio of coal used needs to be supposed or needs to be determined in a partially unfixed state. The present invention is applicable even in this case and can provide coke with the best quality in known information.

The above-mentioned embodiments show the case where the present invention is applied to a coal mixture which is a major raw material for cokemaking and which contains a plurality of coals. The present invention is applicable to other blended raw materials such as oil coke, pitch, and other organic materials in principle.

As described above, a coal mixture which cannot be obtained by any conventional method and which has preferred quality including the compatibility between coals can be obtained by a method according to the present invention. The use of the mixture enables coke with high strength to be produced.

Example 1

Inventive Example 1

A coal mixture was prepared by mixing two or more types of coals with different surface tensions. Upon using the prepared coal mixture as a portion of a coal blend for cokemaking, the blending ratio of each coal contained in the coal mixture was adjusted such that the surface tension of a semicoke mixture obtained from the coals contained in the coal mixture was within a predetermined range from the weighted-average of the surface tensions of semicokes obtained from coals contained in the rest of the coal blend excluding the coal mixture. Coke was produced using the coal mixture adjusted in blending ratio in the coal blend.

First, various properties of semicokes obtained by thermally treating the coals making up the coal mixture were measured. The various properties include the surface tension used in the present invention and characteristics not particularly necessary to carry out the present invention, that is, the mean maximum reflectance of vitrinite Ro and the Gieseler maximum fluidity MF. The mean maximum reflectance of vitrinite Ro of each coal was measured in accordance with JIS M 8816 and the Gieseler maximum fluidity MF thereof was measured in accordance with JIS M 8801. Incidentally, the coals had different surface tensions because the coals were obtained from a single mine and however were produced from different coal seams.

Each coal was thermally treated at 500° C. in an inert gas, was quenched in such a way that the coal was immersed in liquid nitrogen together with a thermal treatment vessel, and was then crushed to 150 μm or less at room temperature, followed by drying at 120° C. for 2 hours in a nitrogen flow, whereby semicoke was obtained. The semicoke obtained from each coal was used as a sample for measuring the surface tension by a film floatation method. The surface tension distribution of the semicokes was measured. The average of the surface tensions in the distribution was used as the typical surface tension of the sample. A liquid used for surface tension measurement was an aqueous solution of ethanol.

The coals making up the coal mixture were those obtained from six types of coal seams. For the coals, Ro was 1.09 to 1.12 and log MF was 2.50 to 2.60. The semicokes obtained from the coals had a surface tension of 36.0 mN/m to 42.5 mN/m. Properties of the six types of coals (Coals 1 to 6) are shown in Table 1.

TABLE 1

| Coal brand | Ro [—] | logMF [logddpm] | γ [mN/m] |
| --- | --- | --- | --- |
| Coal 1 | 1.12 | 2.50 | 36.0 |
| Coal 2 | 1.09 | 2.60 | 38.2 |
| Coal 3 | 1.10 | 2.55 | 40.1 |
| Coal 4 | 1.10 | 2.54 | 40.6 |
| Coal 5 | 1.11 | 2.52 | 41.2 |
| Coal 6 | 1.09 | 2.56 | 42.5 |

Other coals (coals contained in the rest of a coal blend) to be used in a coal blend for cokemaking together with the coal mixture and semicokes thereof were measured for various properties by the above methods. Properties of each coal are shown in Table 2.

TABLE 2

| Coal brand | Ro [—] | logMF [logddpm] | γ [mN/m] | Blending ratio in rest of coal blend [mass percent] |
| --- | --- | --- | --- | --- |
| C Coal | 0.68 | 4.11 | 41.1 | 8 |
| D Coal | 0.82 | 4.43 | 39.9 | 2 |
| E Coal | 0.98 | 2.88 | 40.2 | 28 |
| F Coal | 0.99 | 1.15 | 40.9 | 1 |
| G Coal | 1.10 | 3.69 | 40.6 | 21 |
| H Coal | 1.24 | 1.66 | 40.5 | 11 |
| I Coal | 1.29 | 1.04 | 40.6 | 27 |
| J Coal | 1.62 | 1.28 | 37.8 | 2 |

Next, in the case where the coal mixture accounted for 20% by mass of the coal blend for cokemaking, the coal composition of the rest of the coal blend was determined. The composition of the rest of the coal blend was determined using the average of Ro and the average of log MF of the six types of coals in the coal mixture such that the weighted-average of Ro and the weighted-average of log MF of the individual coals contained in the whole coal blend, which contained the rest of the coal blend and the coal mixture, were 1.10 and 2.50, respectively. The blending ratio (% on a dry mass basis) of each coal in the rest of the coal blend is shown in Table 2. In this operation, the weighted-average of the surface tensions of the semicokes obtained from the coals contained in the rest of the coal blend was 40.5 mN/m. On the basis of this data, the blending ratio of the coal mixture was adjusted using the surface tension of the semicoke mixture obtained from the coal mixture as an indicator, that is, such that the surface tension of the semicoke mixture was 40.5±1.5 mN/m (within the range of 39.0 to 42.0).

From the six types of coal, three types of coal having a surface tension of each semicoke therefrom of 40.1 mN/m, 40.6 mN/m, or 42.5 mN/m, respectively, were chosen. A coal mixture (Coal Mixture 1) was prepared by mixing the three types of coals such that the calculated weighted-average of the surface tension of the semicoke mixture was 40.5 mN/m. The surface tension of the semicoke mixture obtained from the coal mixture measured 40.6 mN/m.

The coal blend for cokemaking was obtained by mixing 20% (% on a dry mass basis) of Coal Mixture 1 with 80 (% on a dry mass basis) of the rest of the coal blend that had a composition shown in Table 2. The coal blend was adjusted such that the content of particles with a size of 3 mm or less was 100% by mass and the content of moisture was 8% by mass. In an electric furnace, 16 kg of the coal blend was provided at a bulk density of 750 kg/m$^3$, followed by carbonization. After carbonization was performed at a furnace wall temperature of 1,100° C. for 6 hours, nitrogen cooling was performed and the drum strength index was measured. The drum strength index DI150/15 was measured by a drum strength measurement method in accordance with JIS K 2151. The strength (JIS DI150/15) of obtained coke was 85.0, which was a level not problematic for use in blast furnaces.

Inventive Example 2

In the rest of the coal blend described above, the surface tension of semicoke obtained from one type of coal (E Coal) having the maximum blending ratio was 40.2 mN/m and did not differ significantly from the weighted-average (40.5 mN/m) of the surface tensions of all the coals contained in the rest of the coal blend. The weighted-average of the surface tensions of several types of semicokes obtained from several types of coals (E Coal and I Coal) that were selected from brands in the rest of the coal blend in ascending order of blending ratio such that the sum of the mass contents in the rest of the coal blend was 55% by mass was 40.4 mN/m. The value 40.4 did not differ significantly from the weighted-average (40.5 mN/m) of the surface tensions of semicokes obtained from all the coals contained in the rest of the coal blend and was within the range of ±1.5 mN/m from the weighted-average (40.5) thereof. Accordingly, on the basis of a standard of Inventive Example 2, the coal mixture which was prepared in Inventive Example 1 and which was used as a source of the semicoke mixture in which the weighted-average of the surface tensions was 40.6 mN/m is preferred in order to produce coke with high strength.

Inventive Example 3

As with Inventive Example 1, the surface tension of semicoke was measured and coke was produced. In Inventive Example 3, the change in strength of coke was investigated in such a way that the surface tension of a semicoke mixture was varied by varying the mixing ratio of the coals (Coals 1 to 6) obtained from the six types of coal seams described in Inventive Example 1 and the difference (difference in surface tension) between the weighted-average of the surface tensions of semicokes obtained from coals contained in the rest of a coal blend and the surface tension of a semicoke mixture was thereby varied. The blending ratios of Coals 1 to 6 in each prepared coal mixture and coal properties determined by weighted-averaging are shown in Table 3. Furthermore, the strength of coke produced from a coal blend, obtained by mixing 20 (mass percent) of the coal mixture with 80 (mass percent) of the rest of the coal blend, by substantially the same method as that described in Inventive Example 1 is shown in Table 4. Table 4 further shows the difference in surface tension between the semicoke mixture obtained from the coal mixture and semicoke obtained from the rest of the coal blend, the interfacial tension $\gamma_{AB}$ therebetween, and the interfacial tension $\gamma_{blend}$ of semicoke obtained from the coal blend. Incidentally, in Inventive Example, coke was measured for coke strength after $CO_2$ reaction in accordance with ISO 18894. FIG. 1 shows the change in the coke strength index JIS DI150/15 due to a difference in surface tension.

TABLE 3

| Coal brand | Coal mixture 1 | Coal mixture 2 | Coal mixture 3 | Coal mixture 4 | Coal mixture 5 | Coal mixture 6 | Coal mixture 7 | Coal mixture 8 |
|---|---|---|---|---|---|---|---|---|
| Coal 1 | 0 | 0 | 10 | 0 | 10 | 2 | 30 | 35 |
| Coal 2 | 0 | 0 | 25 | 0 | 40 | 5 | 25 | 35 |
| Coal 3 | 55 | 30 | 30 | 5 | 45 | 0 | 30 | 30 |
| Coal 4 | 35 | 20 | 25 | 10 | 5 | 0 | 15 | 0 |
| Coal 5 | 0 | 30 | 10 | 30 | 0 | 0 | 0 | 0 |
| Coal 6 | 10 | 20 | 0 | 55 | 0 | 93 | 0 | 0 |
| Weighted-average γ [mN/m] | 40.5 | 41.0 | 39.5 | 41.8 | 39.0 | 42.2 | 38.5 | 38.0 |
| Weighted-average Ro [%] | 1.10 | 1.10 | 1.10 | 1.10 | 1.10 | 1.09 | 1.10 | 1.10 |
| Weighted-average logMF [logddpm] | 2.55 | 2.54 | 2.55 | 2.55 | 2.56 | 2.56 | 2.55 | 2.55 |

TABLE 4

| | Coal blend | | | | | | | |
|---|---|---|---|---|---|---|---|---|
| | Coal blend 1 | Coal blend 2 | Coal blend 3 | Coal blend 4 | Coal blend 5 | Coal blend 6 | Coal blend 7 | Coal blend 8 |
| Coal mixture contained in coal blend | Coal mixture 1 | Coal mixture 2 | Coal mixture 3 | Coal mixture 4 | Coal mixture 5 | Coal mixture 6 | Coal mixture 7 | Coal mixture 8 |
| Difference in surface tension [mN/m] | 0.0 | 0.5 | 1.0 | 1.3 | 1.5 | 1.7 | 2.0 | 2.5 |
| Interfacial tension $\gamma_{AB}$ [mN/m] | 0.000 | 0.004 | 0.016 | 0.028 | 0.036 | 0.047 | 0.065 | 0.101 |
| Interfacial | 0.009 | 0.012 | 0.026 | 0.019 | 0.029 | 0.031 | 0.047 | 0.054 |

TABLE 4-continued

| | Coal blend | | | | | | | |
|---|---|---|---|---|---|---|---|---|
| | Coal blend 1 | Coal blend 2 | Coal blend 3 | Coal blend 4 | Coal blend 5 | Coal blend 6 | Coal blend 7 | Coal blend 8 |
| tension $\gamma_{blend}$ [mN/m] | | | | | | | | |
| Coke strength JIS DI150/15 [—] | 85.0 | 84.9 | 84.9 | 84.8 | 84.6 | 84.0 | 83.6 | 83.2 |
| CSR [%] | 60.3 | 60.0 | 60.1 | 59.8 | 59.5 | 57.5 | 56.2 | 55.0 |

From FIG. 1, it is clear that the reduction in strength is large when the difference in surface tension is more than about 1.5 mN/m. Incidentally, the interfacial tension $\gamma_{AB}$ shown in Table 4 was determined by substituting the weighted-average of the surface tensions of the semicokes obtained from the coals contained in the rest of each coal blend and the surface tension of the semicoke mixture into $\gamma_A$ and $\gamma_B$, respectively, in Equation (3) described above. Furthermore, the interfacial tension $\gamma_{blend}$ shown in Table 4 was determined by substituting the blending ratios of the coals making up each coal mixture, the surface tensions of semicokes obtained from the coals, the blending ratios of the coals in the rest of the coal blend, and the surface tensions of semicokes obtained from these coals into Equation (4). From Table 4, it is clear that a blend with an interfacial tension $\gamma_{AB}$ of 0.036 mN/m or less (particularly a $\gamma_{AB}$ of 0.028 (≈0.03) mN/m or less) has high coke strength. Likewise, it is clear that a blend with an interfacial tension $\gamma_{blend}$ of 0.029 (≈0.03) mN/m or less has high coke strength.

Comparative Example

A coal mixture was prepared by mixing three types of coals (Coals 1 to 3) instead of the coal mixture used in Inventive Example 1. Incidentally, the coal mixture was blended with the rest of a coal blend on the basis of the mean maximum reflectance of vitrinite Ro and the common logarithm log MF of the Gieseler maximum fluidity without particularly using the surface tension of a semicoke mixture obtained by thermally treating the coal mixture as an indicator during mixing. That is, the coal blend was obtained such that the weighted-average of Ro of individual coals contained in the whole coal blend was 1.10 and the weighted-average of log MF thereof was 2.55.

Coke was produced under substantially the same conditions as those described in Inventive Example 1 using the coal mixture. The strength of the obtained coke was 83.2, which was low as compared to Inventive Example 1. The reason why the strength was reduced whereas the coal mixtures prepared in Inventive Example 1 and the comparative example using three types of coals had substantially the same Ro and log MF value is that the difference between the surface tension of the semicoke mixture and the surface tension of the semicoke obtained from each coal in the rest of the coal blend is large and the blending ratios of the coals were not adjusted using the weighted-average of the semicokes obtained from the coals in the coal mixture as an indicator. Actually, in this blend, the difference between a value obtained by weighted-averaging the surface tensions of the semicokes obtained from the coals making up the rest of the coal blend and a value obtained by weighted-averaging the surface tensions of the semicokes obtained from the coals making up the coal mixture is 2.5 mN/m. It has been confirmed that the reduction in strength is large when the difference between these values is more than about 1.5 mN/m.

As described above, according to the present invention, it has been confirmed that in the case of using a coal mixture containing a plurality of coals as a portion of a coal blend for cokemaking, the blending ratios of the coals in the coal mixture can be adjusted in such a way that the coal mixture is prepared using the surface tension of a semicoke mixture prepared by mixing semicokes obtained from the coals in the coal mixture as an indicator, thereby enabling coke with desired strength to be produced.

Example 2

Semicoke samples were prepared from Coals K and L at different thermal treatment temperatures by substantially the same method as that described in Inventive Example 1 and were measured for surface tension. The results are shown in Table 5. From Table 5, it is recognized that the surface tension tends to increase with an increase in thermal treatment temperature in at temperatures of 350° C. or higher. However, the difference in surface tension between two types of semicokes prepared at the same thermal treatment temperature is substantially constant and the magnitude relationship in surface tension between different coals was not varied by varying the preparation temperature of semicoke. Thus, for a method according to the present invention, it is preferred that the thermal treatment temperature at which semicoke is prepared ranges from 350° C. to 800° C. Incidentally, in consideration of the thermal treatment temperature dependence of surface tension, it is preferred all coals used for blending are treated at substantially the same thermal treatment temperature and are evaluated for surface tension.

TABLE 5

| | Thermal treatment temperature (° C.) | | | | | |
|---|---|---|---|---|---|---|
| | 350 | 400 | 450 | 500 | 600 | 800 |
| Surface tension of semicoke obtained from Coal K [mN/m] | 31.9 | 33.0 | 35.5 | 41.1 | 45.2 | 52.3 |
| Surface tension of semicoke obtained from Coal L [mN/m] | 29.8 | 30.4 | 32.4 | 37.6 | 42.2 | 48.7 |

As described above, according to the present invention, it has been confirmed that in the case of using a coal mixture containing a plurality of coals as a portion of a coal blend for cokemaking, the blending ratios of the coals in the coal mixture can be adjusted in such a way that the coal mixture is prepared using the surface tension of a semicoke mixture prepared by mixing semicokes obtained from the coals in the coal mixture as an indicator, thereby enabling coke with desired strength to be produced.

The invention claimed is:

1. A method for preparing a coal mixture for cokemaking, the coal mixture containing two or more types of coals with different surface tensions, the method comprising:
adjusting a blending ratio of each of the coals using a surface tension of a semicoke mixture obtained from the coal mixture as an indicator; and
blending the two or more types of coals according to the adjusted blending ratio to create the coal mixture, the coal mixture being mixed with other coal to create a coal blend for cokemaking;
wherein the adjusting comprises adjusting the blending ratio such that the surface tension of the semicoke mixture is within the range of ±1.5 mN/m from a surface tension of semicoke obtained by thermally treating the other coal.

2. The method according to claim 1, wherein the surface tension of the semicoke mixture is a value that is determined by weighted-averaging surface tensions of two or more types of semicokes using the blending ratios of the coals contained in the coal mixture as weights, the two or more types of semicokes being obtained by thermally treating the coals contained in the coal mixture.

3. The method according to claim 1, wherein the surface tension of the semicoke obtained by thermally treating the rest of the coal blend is a value that is determined by weighted-averaging the surface tensions of semicokes obtained by thermally treating at least two types of coals contained in the rest of the coal blend using the blending ratios of the at least two types of coals contained in the rest of the coal blend as weights.

4. The method according to claim 1, wherein the surface tension of the semicoke obtained by thermally treating the rest of the coal blend is a surface tension of semicoke obtained by thermally treating one type of coal of at least one type of coal contained in the rest of the coal blend, the content of the one type of coal being highest.

5. The method according to claim 1, wherein the surface tension of the semicoke obtained by thermally treating the rest of the coal blend is a value that is determined by weighted-averaging the surface tensions of plural types of semicokes using the blending ratios of the plural types of coals as weights, the plural types of semicokes being obtained by thermally treating plural types of coals contained in the rest of the coal blend, the sum of the mass contents of the plural types of coals being 50% by mass or more.

6. A method for preparing a coal mixture for cokemaking, the coal mixture containing two or more types of coals with different surface tensions, the method comprising:
adjusting a blending ratio of each of the coals using a surface tension of a semicoke mixture obtained from the coal mixture as an indicator; and
blending the two or more types of coals according to the adjusted blending ratio to create the coal mixture, the coal mixture being mixed with other coal to create a coal blend for cokemaking;
wherein the adjusting comprises adjusting the blending ratio such that the semicoke mixture has such a surface tension that the interfacial tension between the semicoke mixture and semicoke obtained by thermally treating one type of coal of at least one type of coal contained in the other coal, the mass content of the one type of coal being 50% by mass or more, is 0.03 mN/m or less.

7. The method according to claim 6, wherein the interfacial tension is calculated by the following equation:

[Math. 2]

$$\gamma_{AB}=\gamma_A+\gamma_B-2\phi\sqrt{\gamma_A\gamma_B} \qquad (2)$$

where
$\gamma_A$ is a surface tension of the semicoke obtained by thermally treating the one type of coal,
$\gamma_B$ is a surface tension of the semicoke mixture,
$\gamma_{AB}$ is a interfacial tension, and
$\phi$ is an interaction coefficient.

8. The method according to claim 6, wherein the Interfacial tension is calculated by the following equation:

[Math. 3]

$$\gamma_{AB}=\gamma_A+\gamma_B-2\exp[-\beta(\gamma_A-\gamma_B)^2]\sqrt{\gamma_A\gamma_B} \qquad (3)$$

where
$\gamma_A$ is a surface tension of the semicoke obtained by thermally treating the one type of coal,
$\gamma_B$ is a surface tension of the semicoke mixture,
$\gamma_{AB}$ is a interfacial tension, and
$\beta$ is a constant.

9. A method for preparing a coal mixture for cokemaking, the coal mixture containing two or more types of coals with different surface tensions, the method comprising:
adjusting a blending ratio of each of the coals using a surface tension of a semicoke mixture obtained from the coal mixture as an indicator; and
blending the two or more types of coals according to the adjusted blending ratio to create the coal mixture, the coal mixture being mixed with other coal to create a coal blend for cokemaking,
wherein the adjusting comprises adjusting the blending ratio such that the semicoke mixture has such a surface tension that the interfacial tension between the semicoke mixture and plural types of semicokes obtained by thermally treating plural types of coals in the other coal, the sum of the mass contents of the plural types of coals being 50% by mass or more, is 0.03 mN/m or less.

10. The method according to claim 9, wherein the interfacial tension is calculated by the following equation:

[Math. 2]

$$\gamma_{AB}=\gamma_A+\gamma_B-2\phi\sqrt{\gamma_A\gamma_B} \qquad (2)$$

where
$\gamma_A$ is a surface tension of the plural types of semicokes,
$\gamma_B$ is a surface tension of the semicoke mixture,
$\gamma_{AB}$ is a interfacial tension, and
$\phi$ is an interaction coefficient.

11. The method according to claim 9, wherein the interfacial tension is calculated by the following equation:

[Math. 3]

$$\gamma_{AB}=\gamma_A+\gamma_B-2\exp[-\beta(\gamma_A-\gamma_B)^2]\sqrt{\gamma_A\gamma_B} \qquad (3)$$

where
$\gamma_A$ is a surface tension of the plural types of semicokes,
$\gamma_B$ is a surface tension of the semicoke mixture,
$\gamma_{AB}$ is a interfacial tension, and
$\beta$ is a constant.

12. A method for preparing a coal mixture for cokemaking, the coal mixture containing two or more types of coals, the method comprising:
   determining a blending ratio of the coal mixture in the coal blend in advance in the case of using the coal mixture being as a portion of the coal blend;
   determining a type and a blending ratio of coal contained in the rest of the coal blend excluding the coal mixture; and
   adjusting the blending ratio of each coal in the coal mixture such that the interfacial tension ($\gamma_{blend}$) of semicoke obtained by thermally treating the coal blend is 0.03 mN/m or less.

13. The method according to claim 1, wherein the interfacial tension is determined by a film floatation method.

14. A coal mixture produced by the preparation method according to claim 1.

15. A method for producing coke, comprising:
   blending the coal mixture according to claim 1 with the other coal to create the coal blend; and
   carbonizing the coal blend to form the coke.

* * * * *